United States Patent
Swersey et al.

(10) Patent No.: US 6,843,106 B2
(45) Date of Patent: Jan. 18, 2005

(54) DIFFERENTIAL PERMEOMETER

(75) Inventors: Burt Swersey, Stephentown, NY (US); Marcie J. Harvey, Pearland, TX (US); Elias Kaplan, Redmond, WA (US); Jennifer Lamana, Troy, NY (US); Stephen J. Howard, Troy, NY (US); Dean Meloney, Troy, NY (US); John P. Weed, Port St. Lucie, FL (US); Timothy Novak, Troy, MI (US)

(73) Assignee: Rensselaer Polytechnic Institute, Troy, NY (US)

( * ) Notice: Subject to any disclaimer, the term of this patent is extended or adjusted under 35 U.S.C. 154(b) by 616 days.

(21) Appl. No.: 09/800,872

(22) Filed: Mar. 7, 2001

(65) Prior Publication Data

US 2002/0178790 A1 Dec. 5, 2002

Related U.S. Application Data

(60) Provisional application No. 60/187,931, filed on Mar. 8, 2000.

(51) Int. Cl.$^7$ .............................................. G01N 15/08
(52) U.S. Cl. ......................................................... 73/38
(58) Field of Search .............................................. 73/38

(56) References Cited

U.S. PATENT DOCUMENTS

| | | | | |
|---|---|---|---|---|
| 3,618,361 A | * | 11/1971 | Stephens et al. ................ 73/38 |
| 4,191,046 A | * | 3/1980 | Baker et al. ..................... 73/38 |
| 4,384,474 A | * | 5/1983 | Kowalski ......................... 73/38 |
| 4,566,326 A | * | 1/1986 | Lowell ....................... 73/865.5 |
| 4,856,967 A | * | 8/1989 | Jones .......................... 417/342 |
| 5,088,316 A | * | 2/1992 | McKelvey et al. ............. 73/38 |
| 5,107,696 A | * | 4/1992 | Mayer et al. ................... 73/38 |
| 5,503,001 A | * | 4/1996 | Wong ............................. 73/38 |
| 5,544,520 A | * | 8/1996 | Graf et al. ...................... 73/38 |
| 5,906,743 A | * | 5/1999 | Cohen et al. ............. 210/502.1 |
| 5,968,312 A | * | 10/1999 | Sephton ..................... 159/47.1 |

FOREIGN PATENT DOCUMENTS

| | | | | |
|---|---|---|---|---|
| EP | 518250 A1 | * | 12/1992 | ........... B01D/29/11 |
| SU | 787958 | * | 12/1980 | |
| WO | WO 9428393 A1 | * | 12/1994 | .......... G01N/15/08 |

* cited by examiner

*Primary Examiner*—Hezron Williams
*Assistant Examiner*—John Fitzgerald
(74) *Attorney, Agent, or Firm*—Francis C. Hand; Carella, Byrne, Bain (57) ABSTRACT

Permeability of a porous, sheet-like sample is determined using a device that is designed to measure the pressure differential between a first stream of fluid applied across an entire thickness of a test sample and a second stream of fluid applied across an entire thickness of a reference sample. The flow rate for both the test fluid flow system and the reference fluid flow system is determined independently, by measuring a pressure drop throughout the flow system. Data obtained from pressure and flow rate for test and reference fluids are used to calculate percent change in permeability and/or actual permeability using Darcy's Law.

6 Claims, 7 Drawing Sheets

Fig 1 Schematic of Permeometer

Fig 7

Top View of 34

Fig. 6

Side View of 34

DIFFERENTIAL PERMEOMETER

This application claims the benefit of U.S. Provisional Application No. 60/187,931, now filed on Mar. 8, 2000.

This invention relates to a differential permeameter. More particularly, this invention relates to a differential permeameter for the measurement of fluid permeability through a porous, sheet-like sample.

BACKGROUND OF THE ART

Material fluid permeability is an essential quality measurement in a variety of industries including textiles and papermaking. Permeability in itself is related to the porosity, density, and thickness of a material. Consistency of these material properties over time is required within a process as an indication of the quality. The purpose of permeability measurement is to accurately indicate the quality and consistency of a material product.

Historically, airflow permeability measurement devices have followed one of two basic genres: series or bridge. The bridge method, exemplified by Gurley Precision Instruments Co. [of Troy, N.Y.] Permeometer, compares pressure drops across two streams with a single vacuum source. One flow stream passes through a variable valve, comparator chamber, and fixed orifice to the reservoir, while the second passes through the unknown sample material, test chamber, and variable micrometer orifice into the reservoir. Orifices are varied until the pressure drop across the variable orifice is fixed at 0.5 inches of water and the pressures in both the test chamber and comparator chamber are equal, thus the pressure drop across the unknown sample is also 0.5 inches of water.

Among the many assumptions necessary for this measurement is the standard environment. Conditions such as temperature or relative humidity affect various components of permeability measurements. In 1856, Henry Darcy published an equation for the basic relationship of flow through porous media. He discovered that discharge varies directly with head loss over distance, for small discharges. Although recent modifications have been made to the coefficients, the relation has remained the same. Darcy's equation is:

$$h_f = c \frac{\mu V L}{\gamma d^2}$$

(Albertson, et al. *Fluid Mechanics*, p.211–212). Where $h_f$ is head loss, V is the mean velocity of flow, $\mu$ is the fluid absolute viscosity, $\gamma$ is the fluid specific weight, d is the characteristic grain diameter of the porous material, and c is the dimensionless coefficient which describes the porous media by including the size and distribution of grains, the porosity, and the orientation and arrangement of the grains. This is referred to as the coefficient of permeability and is equal to the pressure drop over specific weight. Note that the new flow coefficient $K_D$ if $d^2$ over coefficient c. Rewriting for volumetric flow equal to bulk velocity times area gives:

$$Q = \frac{A \Delta P K_D}{L \mu}$$

It should be noted that density does not enter into the equation of laminar flow through a porous material. For laminar flow, the forces of inertia, which depend on density, are negligible and the forces of viscosity are in complete control. Since viscosity is a fluid property, it does not change with pressure or location within the flow. Flow through a porous material can be characterized by low velocity, high-pressure drop, and very small pore diameter, so the conditions for laminar flow, such as a small Reynolds number, is consistent.

Normalizing the flow constant per unit length, this dependence on viscosity is an inherent dependence on temperature. According to the *Handbook of Chemistry and Physics*, for air, absolute viscosity can be expressed solely as a known function of temperature, linear in the region from 20 to 60 degrees Celsius.

$$Q = \frac{A \Delta P K_N}{\mu}$$

However, air not only flows through this permeable membrane, but also various orifices. Flow through a fixed orifice is generally expressed in the Bernoulli corrected form as $$V = (2gh)^{1/2}$$

(Binder, *Fluid Mechanics*, p. 99). Where h is a head loss, commonly replaced by $\Delta P$ over $\gamma$, and $\gamma$ is the specific weight or fluid density times gravitational constant. Expressed in terms of volumetric flow rate, $$Q = KA \left( \frac{2 \Delta P}{\rho} \right)^{1/2}$$

Where K is a new flow constant, A is the orifice area and $\rho$ is the fluid density. Coefficient K is required because the cross-sectional are A is inconsistent in the flow on fluid through an orifice. Density, however, is much more difficult to specify than absolute viscosity. It requires knowledge of atmospheric pressure, vapor pressure, relative humidity, temperature and precise compressibility. Flow through an orifice is one of the oldest, yet most reliable, methods of measuring and controlling the flow of fluids (Binder), which most likely explains the historical use in permeability measuring devices, however the limitation is in the accurate specification of fluid density.

A permeameter sold by Frazier, Inc. [of Hagerstown, Md.] benchmarks the series method. The device draws a variable suction across the permeable membrane and a fixed but alterable orifice. Pressure drop across the porous sheet-like material is held to a standard, while the pressure drop across the fixed orifice is measured and compared with calibrated results. Once again, problems arise with changes in atmosphere. Changes in temperature, pressure, humidity, et cetera, between the conditions at calibration and the conditions at measurement will cause error in results.

The simple series device above is governed by Darcy's Law and flow through an orifice. Equating, the normalized permeability constant for a particular sample test section may then be determined as follows $$K_N = \frac{K_{orifice} A_{orifice} \mu \left( \frac{2 \Delta P_{orifice}}{\rho} \right)^{1/2}}{A_{membrane} \Delta P_{membrane}}.$$

Solving and combining with Darcy's Law at standardized conditions yields the industrial standard permeability. The result is, once again, dependent upon temperature, through viscosity ($\mu$) and further atmospheric conditions such as humidity, through density ($\rho$).

Permeability measurement has been a necessary quality control measurement in industry, including textile and paper industries. The measurement issued as a fault detection platform across a web product span and between successive products or webs. The main goal is to detect errors or inconsistencies in a product or web, indicating process malfunction or necessary web replacement due to use. For example, U.S. Pat. No. 4,495,796 uses an ad hoc permeability measurement as mechanical error detection following a cigarette paper perforation device. U.S. Pat. No. 5,436,971 describes a device for measuring air permeability across a textile to find manufactured, woven inconsistencies.

Single chamber designs have been developed as well, Such as described in U.S. Pat. Nos. 4,756,183 and 4,991,425, both of which are single chamber devices that ignore the change in permeability due to temperature change.

Most devices patented to this point ignore flow changes due to atmospheric conditions. These devices assume that all measurements are taken at standard conditions, which though desirable, is neither consistently practiced nor universally practical for industrial use.

U.S. Pat. No. 4,649,738 takes atmospheric changes into consideration while integrating high-speed permeability measurements in an industrial process. The sample focused on is cotton at various stages of the cotton ginning process. The device measures differentially over a measurement stream and reference stream. The device does not, however, measure across an entire sample, use a reference sample, or provide an accuracy level that is needed in most applications. The device is also specific to the measurement of a continuous flow of cotton, and sheet-like materials cannot be measured using the present cofiguration.

It is clear that changes in atmospheric conditions will cause alteration of standard expected flows, in differing amounts between an orifice and a permeable membrane. Thus, measured pressure drop for a single material will change as atmospheric conditions change. Removal of the dependence of these conditions on the measurement of permeability will therefore vastly improve the accuracy of measurement.

It is an object of the invention is to provide a method and device of measuring differential permeability that eliminates environmental factors and measures permeability accurately by measuring the differential pressure drop across a fluid flow after flowing through a test sample and the fluid flow after flowing through a reference sample.

It is another object of this invention to increase the limits of permeability measurement accuracy.

It is another object of this invention to introduce the theory of differential measurement across two samples to determine the permeability of a porous material.

It is another object of this invention to eliminate variations in results of permeability measurements due to a changing environment.

It is another object of this invention to increase permeability measurement accuracy by changing the required range of gauge measurement.

SUMMARY OF THE INVENTION

Briefly, the invention extends from the basic concept of flaw detection. This method of measurement compares two porous sheet-like samples across their entire thickness in order to detect flaw, or difference, between the two samples.

The invention provides a permeameter, which is comprised of:
 a. A test head having a surface in communication with the test material;
 b. A reference head having a surface in communication with the reference material;
 c. A clamping device for both the test sample and reference sample;
 d. At least one flow measurement device, such as an orifice plate in the test fluid flow system;
 e. At least one flow measurement device, such as an orifice plate in the reference fluid flow system which is identical to the test orifice plate;
 f. An applied fluid supply;
 g. A means for measuring the pressure differential between the test fluid stream and the reference fluid stream;
 h. A means for measuring the fluid flow in both the test fluid flow system and the reference fluid flow system;
 i. A honeycomb-type device placed in each flow system to promote laminar flow and eliminate swirl;

The invention further provides a method for determining data to calculate permeability of a test sample comprised of the following steps:
 a. Place the sheet-like reference sample of known or desirable permeability in the reference-clamping device and in communication with the reference fluid flow system;
 b. Supply a fluid flow stream across both test and reference samples, so that the pressure drop across both samples is (very near to) a fixed standard;
 c. Measure the fluid flow through the test fluid flow system by measuring the pressure drop across a flow device, such as an orifice plate; within the test fluid flow system.
 d. Measure the fluid flow through the reference fluid flow system by measuring the pressure drop across a flow device, such as an orifice plate; within the reference fluid flow system.
 e. Measure the pressure differential between the test fluid stream and the reference fluid stream and calculate the permeability of the test sample by using the differential pressure across the test fluid flow stream, the known permeability of the reference sample, and the air flow through both the test fluid flow system and the reference fluid flow system.

Further objects and advantages of our invention will become apparent from a consideration of the ensuing description taken in conjunction with the accompanying drawings wherein:

DESCRIPTION

Figure 1:
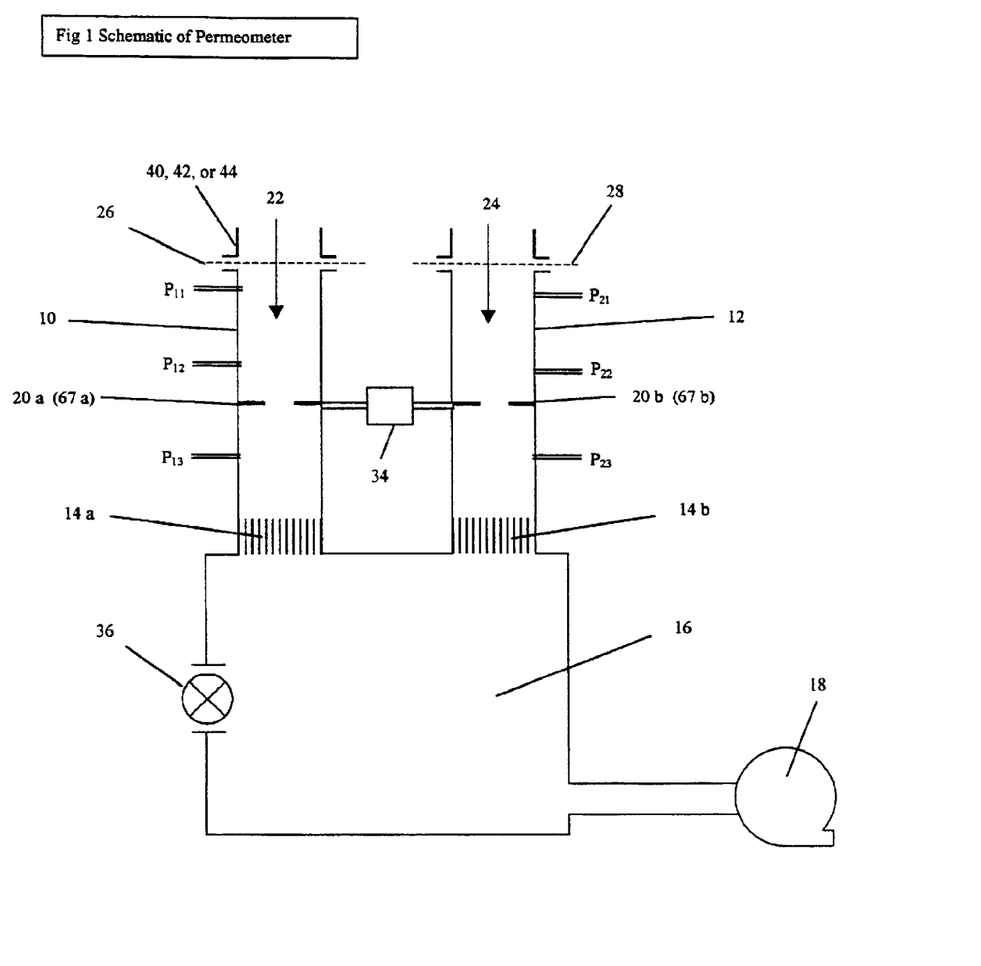
FIG. 1 is a simplified schematic illustration of a permeameter constructed in accordance with the invention.

Referring to FIG. 1, the permeometer includes a test fluid flow system 10 and a reference fluid flow system 12 which are in the form of tubes and are in common communication with a reservoir system 16. Fluid flow is initiated by a fluid flow initiator 18, for example, a speed-controlled centrifugal fan. The applied fluid used in this embodiment of the apparatus is air. The cross section of each of the test fluid flow system 10, the reference fluid flow system 12 and the reservoir system 16 is circular.

The airflow is very similar through the test fluid flow system 10 and the reference fluid flow system 12 by the symmetry in diameter between both systems. The cross-sectional area of the joining reservoir system 16 is greater than the sum of the cross-sectional area of system 10 and the cross-sectional area of system 12. Honeycomb structures 14a and 14b are located at the base of both the test fluid flow system 10 and reference fluid flow system 12. Each honeycomb structure consists of ¼-inch diameter pipes in a cluster that fills the inner diameter of both systems 10,12. Both honeycomb diameter and length can vary.

Upstream from the honeycomb structure 14a in the test fluid flow system 10 is an orifice plate 20a. Upstream from the honeycomb structure 14b in the reference fluid flow system 12 is an orifice plate 20b. Each orifice plate creates a measurable pressure drop in the respective fluid flow system 10,12. The measured pressure drop in each fluid flow 22 and 24 is directly proportional to the velocity of that flow, and is used to compute permeability of the test sample. The hole diameters in the respective orifice plates 20a, 20b are always exactly identical. However, both plates can be made to vary in hole size, either by interchanging a pair of fixed, identical orifice plates of one hole diameter for a new pair of fixed, identical orifice plates of a different hole diameter, or by means of the continuously variable orifice system 34 as described below with respect to FIGS. 6 and 7.

Figure 6:
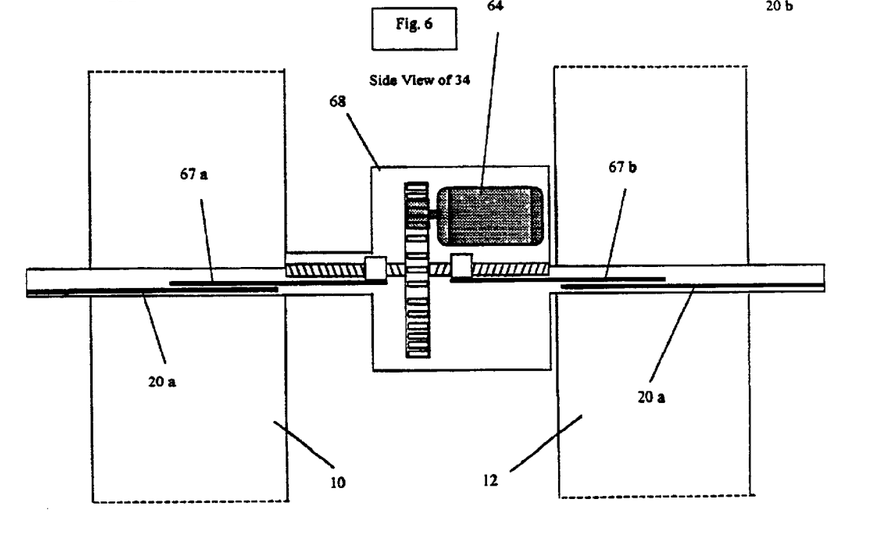
FIG. 6 is a simplified schematic of a variable orifice system in accordance with the invention.
Figure 7:
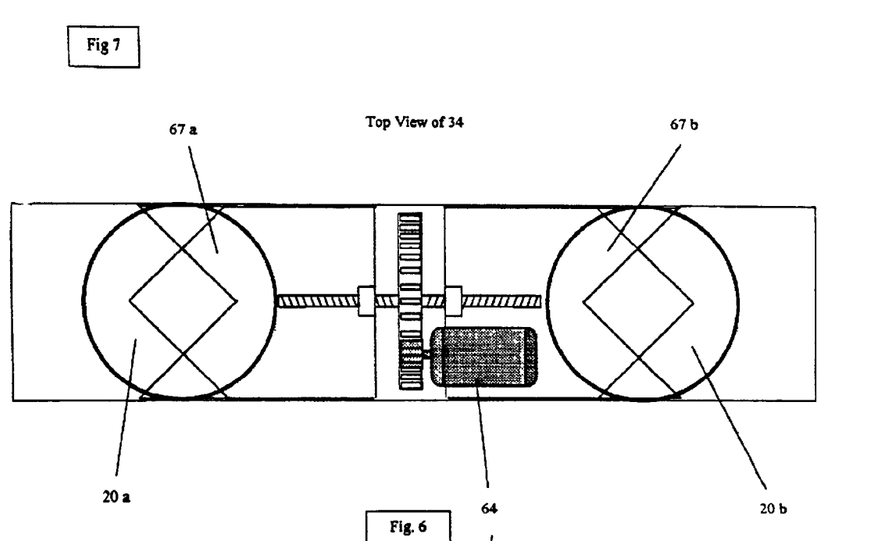
FIG. 7 is a top view of the variable orifice system of FIG. 6.

Referring to FIGS. 6 and 7, a change in orifice diameter is often needed to ensure that the pressure measurements stay within the operational range of the pressure gauges or required standard measurement range. Continuous variation in orifice size is accomplished by sliding an orifice plate 67a, 67b over the plate 20a, 2b using a dual motorized screw drive 64 that is mounted on a bracket 68 in the space between the flow systems 10,12. The sliding action changes the total area of each orifice hole.

In order to use the permeameter, a sheet-like test sample 26 is required. A sheet-like reference sample 28 is also required for percent difference in permeability measurement. The reference sample should have a known permeability or have known desirable characteristics. Samples 26 and 28 can also be similar, yet both unknown, in which case exact percent change in permeability will be measured as a quantified quality/consistency indication. If absolute permeability is the desired measurement, the reference sample 28 should be omitted. The differential pressure difference will read the absolute pressure drop across the test sample 26, and the absolute permeability can be measured.

Figures 3, 3A:
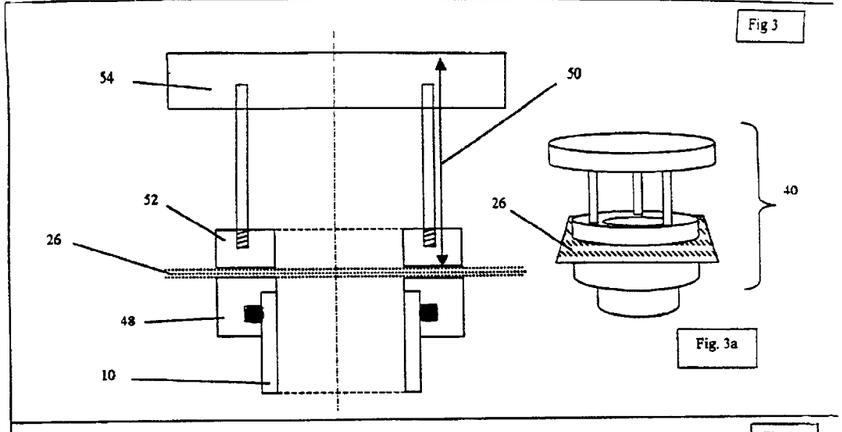
FIG. 3 illustrates a side view of a clamping device employed in the permeameter of FIG. 1.
FIG. 3a illustrates a perspective view of the clamping device of FIG. 3.

Referring to FIGS. 3 and 3a, a test-clamping device 40 is mounted at the upper end of the test fluid flow system 10 so that the entire opening of the system 10 is covered. Likewise, a reference-clamping device 40 is mounted at the upper end of the reference fluid flow system 12 so that the entire opening of the system 12 is covered. For any particular choice of clamping method, the test and reference clamping devices are identical.

Each clamping device 40 is referred to as a direct weight clamping system and is composed of two parts. The first part is a bottom flange 48, the second part is a top flange 50. The bottom flange 48 fits tightly at the entrance of the fluid flow system, and restricts airflow through the outer diameter of the system using an o-ring. The top flange 50 is an unattached piece that serves to apply downward clamping pressure on the test (or reference) sample that is placed in between the flanges 48 and 50. The top flange 50 consists of a lower contact ring 52 with the same outer and inner diameter as the bottom flange 48 and an upper shelf 54 raised three inches The shelf 54 has a purpose of holding accurate weight. This allows for variability of clamping force. The clamping force minimizes lateral fluid leakage through the sample and the flow entrance of each fluid flow system 10 and 12, which can affect the pressure reading and therefore alter the permeability measurement.

Figure 4:
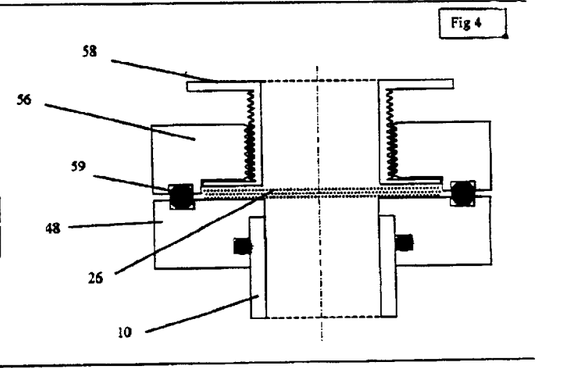
FIG. 4 illustrates a side view of a modified clamping device in accordance with the invention.
Figure 4A:
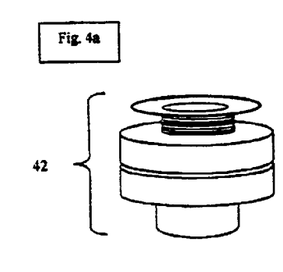
FIG. 4a illustrates a perspective view of the clamping device of FIG. 4.

The top flange 50 is placed on top of the sample such that the outer diameter of the lower contact ring 52 and the outer diameter of bottom flange 48 are aligned. Alternatively, as shown in FIGS. 4 and 4a, a clamping device 42 also referred to as an O-ring clamping system may be used to hold a sample. As shown, the clamping device 42 is composed of two parts. The first part is the bottom flange 48, which is identical to that used in the direct weight clamping system 40, and the second part is a top flange 56. The top flange 56 is an unattached piece that serves to apply downward pressure on a primary O-ring seal 59, which lies in a groove between the flanges 48 and 56.

A screw-down sample holder 58 is a tube that is threaded on its outer surface with the same inner diameter as the bottom flange 48. The lower end of the holder 58 comes in direct contact with the disk-like sample and serves to hold the sample in place. The upper end of the holder 58 has an annular shelf for the purpose of rotating the holder 58 with respect to the top flange 56 so as to adjust the vertical position of the holder 58 and also for holding accurate weight.

The primary O-ring seal 59 eliminates lateral fluid leakage through the circumference of the disk-like sample and thereby makes permeability measurement independent of applied clamping pressure.

Figure 5:
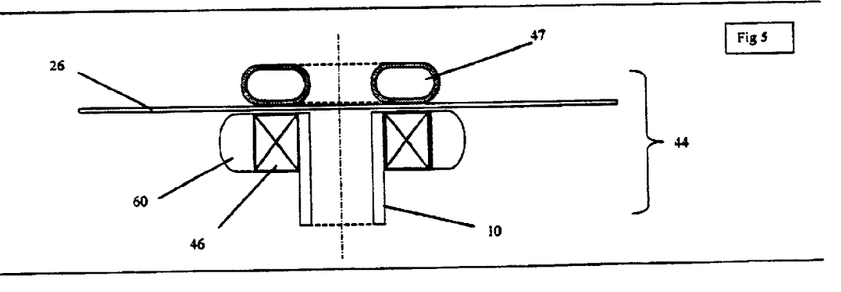
FIG. 5 illustrates a part cross-sectional side view of a magnetic clamping device in accordance with the invention.

Referring to FIG. 5, a clamping device 44 also referred to as a magnetic clamping system may also be used to hold a sample. This clamping device 44 is composed of two parts. The first part is a bottom flange composed of an electromagnet 46 and a fabric guard 60, and the second part is a magnetic clamping ring 47. The magnetic clamping ring 47 is an unattached piece that serves to apply downward pressure on the test sample by means of a magnetic attraction toward the electromagnet 46. The magnetic clamping ring 47 consists of either a lightweight hollow ferrous structure, or a lightweight nonferrous structure that contains internal permanent magnets. The lower surface of ring 47 comes in direct contact with the sheet-like sample and serves to apply clamping pressure that minimizes lateral fluid leakage through the sample. Ring 47 and contacting surfaces of 46 and 60 may be coated with a protective, nondestructive material.

The electromagnet 46 is the source of the magnetic clamping force on the ring 47. By adjusting the electric currents put through the electromagnet, the resulting clamping pressure is thereby varied.

By recording the changing value of measured permeability while simultaneously varying the magnetic clamping pressure in a known way, on a fixed sample, the measurement of permeability in the limit of infinite clamping pressure can be calculated by means of asymptotic analysis. This limiting value is equal to the true permeability of the sheet-like test sample in the ideal case of zero lateral fluid leakage.

Operation (Standard Operation)

Figure 2:
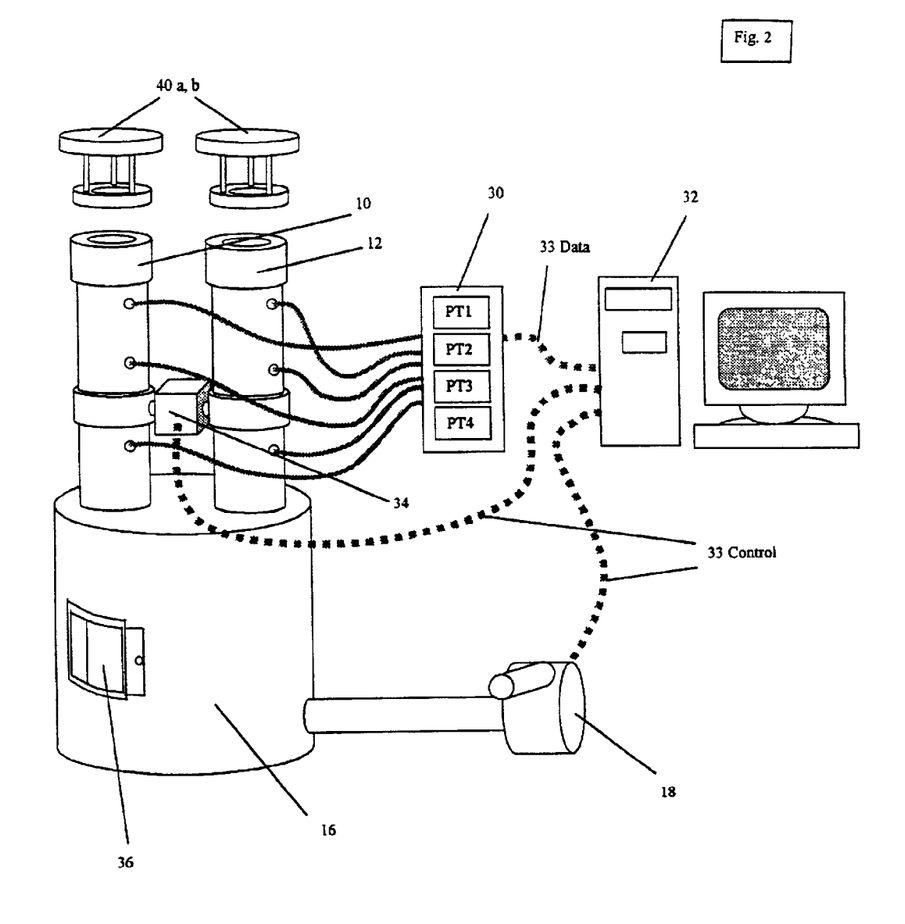
FIG. 2 is an isometric sketch of the permeameter of FIG. 1.

The method of operation of the permeameter is completed with the use of four pressure transducers mounted in a common housing 30 (see FIG. 2). After the test sample 26 and reference sample 28 are manually placed in the corresponding clamping devices such as those described by 40, 42 or 44, the speed of the fluid flow initiator 18 is manually or automatically adjusted by a computer or other data/control system 32, so that the pressure drop across the reference sample is 0.5 inches of water, measured using pressure transducer PT1. The flow is similar through both the test fluid flow system 10 and the reference fluid flow system 12, and therefore the pressure drop across test sample 26 is similar to 0.5 inches of water.

When pressure drop across both samples is steady at approximately a desired standard, the airflow is measured. This is accomplished by measuring the pressure drop across the test orifice plate 20a and the reference orifice plate 20b, due to the fact that air flow is proportional to pressure drop. Pressure transducer PT2 is used to measure the pressure drop ($P_{12}$ minus $P_{13}$) across orifice 20a. Pressure transducer PT3 is used to measure the pressure drop ($P_{22}$ minus $P_{23}$) across orifice plate 20b. The pressure measurement locations $P_{11}$, $P_{12}$, $P_{13}$, $P_{21}$, $P_{22}$, $P_{23}$ are relative locations outlined in FIG. 1.

The small differential pressure between the test fluid flow system 10 and the reference fluid flow system 12 ($P_{11}$ minus $P_{21}$) is measured with high precision using pressure transducer PT4.

The permeability of test sample 26 and the percent difference in permeability between test sample 26 and reference sample 28 are calculated by the data acquisition system 32 using the measurements taken from pressure transducers PT1, PT2, PT3, and PT4, which are sent to the computer as analog signal 33.

As shown, a monitor is connected with the computer 32 to provide a visual display of sample analysis and resultant readings.

Figure 9:
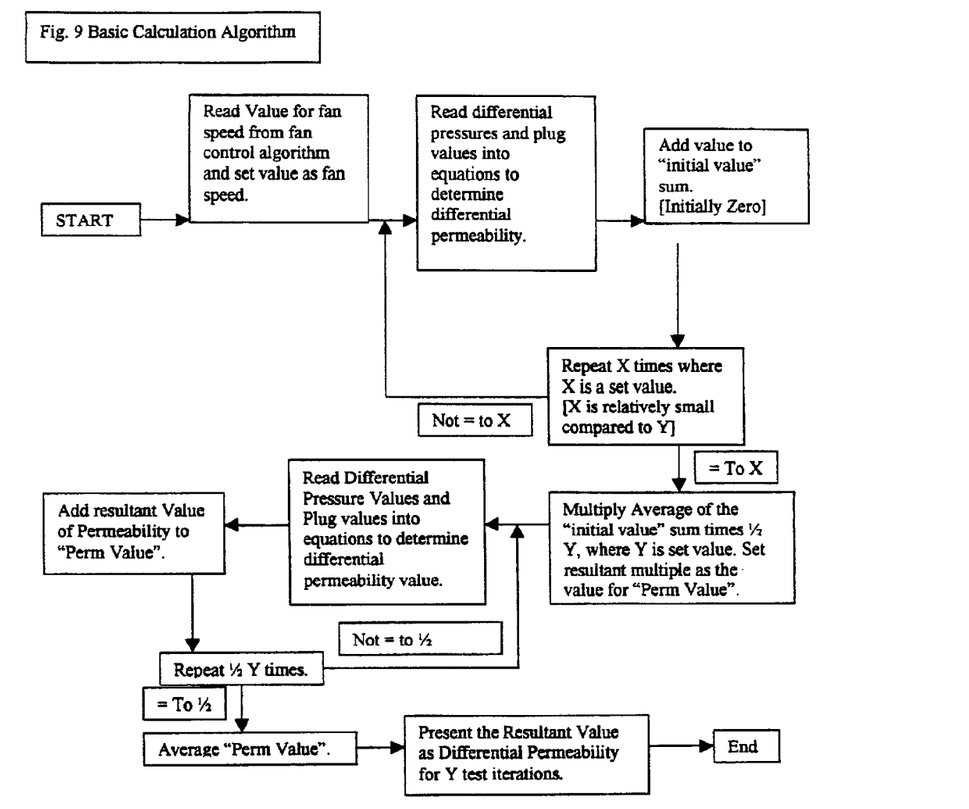
FIG. 9 illustrates an algorithm for a differential permeability control calculation in accordance with the invention.

Standard Algorithms for Adjusting Fan Speed and Variable Orifice Size and Computing Differential Permeability The fan control algorithm begins with an approximate value input by the user, either in the form of a number or in the form of a material quality such as relative strength, material type, and similar information. Beginning with the base value, (which is estimated from user input) the fan is adjusted by adding or subtracting speed until the measured pressure drop between atmospheric pressure and the pressure within the reference tube measures 0.5 inches of water. A basic representation of the Fan Control Algorithm is represented in FIG. 9.

Figures 10, 11:
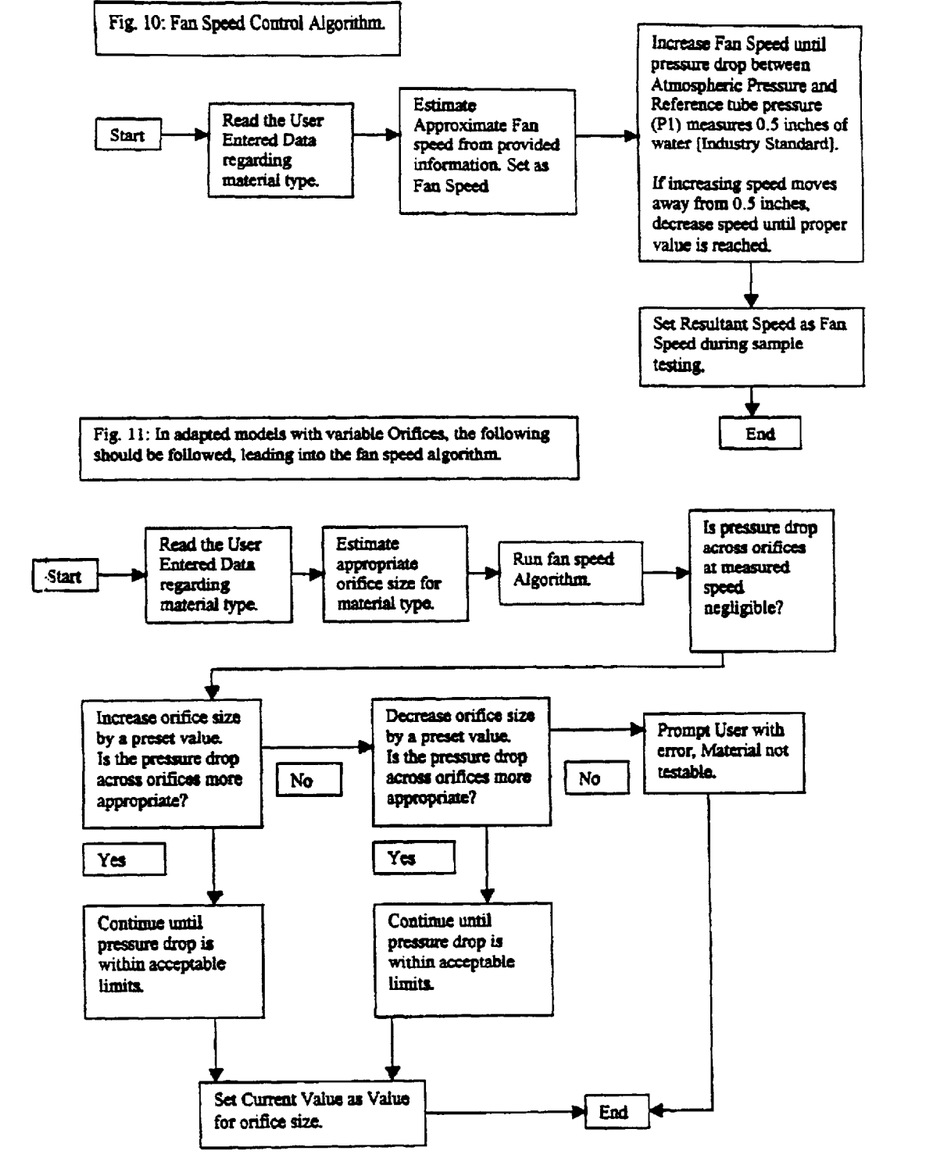
FIG. 10 illustrates an algorithm for fan speed control in accordance with the Invention.
FIG. 11 illustrates an algorithm for fan speed control with a variable orifice in accordance with the invention.

In models with automated variable orifices, a resultant differential permeability value smaller than an acceptable range or an inability to settle on a fan speed due to a lack of a pressure drop would result in an appropriate adjustment of orifice size to form a measurable pressure drop. An example of this is illustrated in FIG. 10.

To determine the test differential permeability quickly, an adjusting algorithm is necessary. First, the algorithm takes a repetition of X permeability readings where X is a set value that is small relative to the overall number of tests to arrive at an initial average reading. The values are then averaged, and the average set as the first half of a number Y of tests. For example, out of Y=300 total tests, the average value would be repeated for the first 150 values. The average of the Y values is then taken and it represents the average differential permeability value for the test. The Variables X and Y are relative to the desired accuracy for test purposes, where Y is the total number of averaging cycles and X is a small percentage of Y. If possible, the algorithm should eliminate the rouge permeability values that naturally occur in the testing process by comparing them to an expected value. For instance, if in comparison to the initial average value, the measured value during testing is of an opposite sign or much larger or smaller (by a order of magnitude) it should be replaced with the initial average value to minimize erroneous readings. The Flowchart representation of the measurement algorithm is illustrated in FIG. 11.

Alternate Operation Procedures

Figure 8:
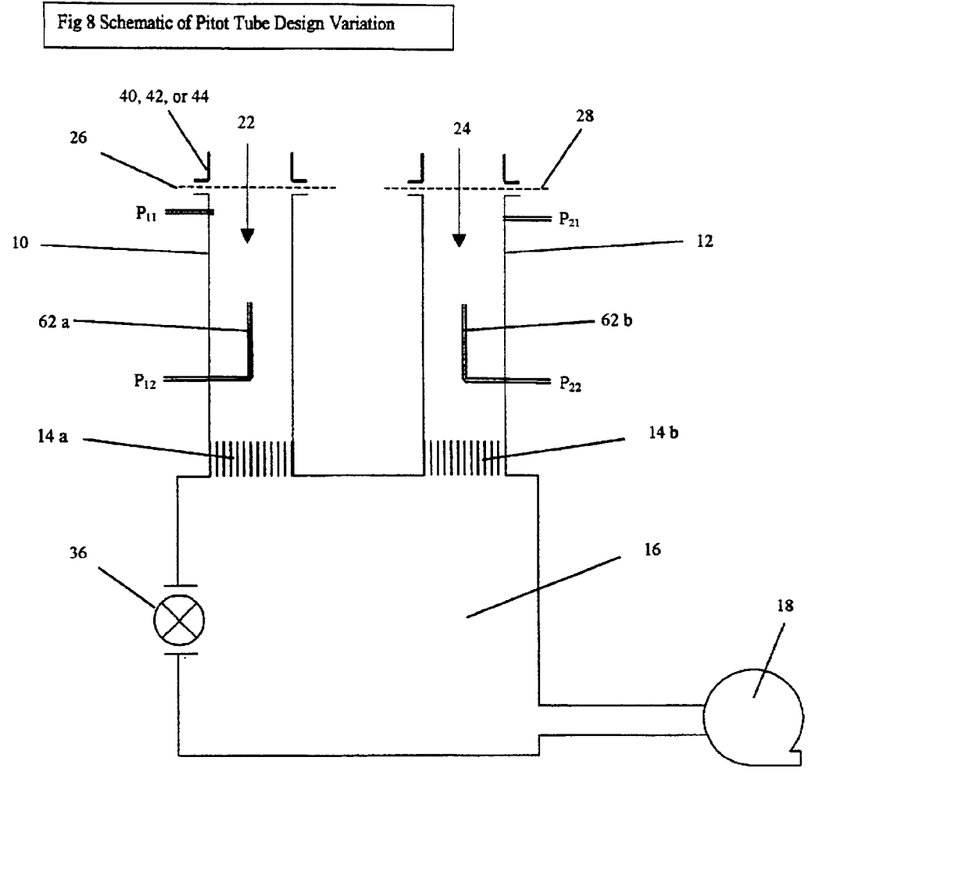
FIG. 8 is a simplified schematic of a Pitot tube construction in accordance with the invention.

The method for operation of the Pitot tube permeameter is completed with the use of three pressure transducers. After the test sample 26 and reference sample 28 are manually placed in the corresponding clamping devices, the speed of the fluid flow initiator 18 is manually or automatically adjusted so the pressure drop across the reference sample and the atmosphere is 0.5 inches of water, measured using pressure transducer PT1. The airflow is similar through both the test fluid flow system 10 and the reference fluid flow system 12, therefore the pressure drop across test sample 26 is similar to 0.5 inches of water.

Once the pressure drop across sample 28 is at 0.5 inches of water, the airflow in each system is measured. This is accomplished by measuring the difference in pressure ($P_{21}$ minus $P_{22}$) between the reference fluid flow system 12 and the Pitot tube 62b with pressure transducer PT2. Then, the small difference in pressure between the Pitot tubes 62a, 62b ($P_{12}$ minus $P_{22}$) is measured with high precision using pressure transducer PT4.

The permeability of the test sample 26 and the percent difference between the test sample 26 and the reference sample 28 are calculated by the data acquisition computer 32 using the measurements taken from pressure transducers PT1, PT2, and PT4, which are sent to the computer 32 as analog signal 33 (see FIG. 2).

Referring to FIG. 8, use may be made of a Pitot tube 62a, 62b to measure fluid flow rate inside the test fluid flow system 10 and the reference fluid flow system 12. As shown, each Pitot tube 62a, 62b is positioned above the respective honeycomb structure 14a, 14b in the respective flow system 10,12 to measure the total pressure in each respective system 10,12.

The fluid flow is initiated by the fluid flow initiator 18 that, in this embodiment, is a speed-controlled fan.

A pressure transducer measures the pressure differential between the Pitot tube 62a and the Pitot tube 62b, yielding $P_{12}$ minus $P_{22}$. The difference in pressure shows a relationship in airflow between the two systems 10 and 12, and is used to compute permeability of the test sample.

Beyond simple air permeability testing, the differential permeameter allows accurate testing with almost any fluid flow, assuming the relative viscosity is low enough. To perform low-viscosity fluid permeability tests, minor device modifications should be considered. While background theories hold for most low viscosity fluids, certain special conditions may apply to fluids that are denser than air. In order to maintain even distribution, the flow systems 10,12 may need to remain in a vertical position to maintain evenly distributed laminar flow (to prevent pooling in areas of the machine) though with most fluids this is unnecessary after proper pressure is generated by the pumping device. In addition, in low viscosity, lower-density fluids such as water; the test fluid can be recycled via a reservoir.

All of the permeameter parts should be appropriate for (non-air) fluid testing, for example, the pressure sensors should be approved for other fluid testing and the pressure fan should be replaced with a variable speed fluid pump. Further special considerations should be taken when working with fluids that are potentially damaging to the apparatus (for example acidic and basic fluids) and appropriate care and or replacements should be practiced.

The fluid immersion differential permeability testing allows for the examination and testing of a variety of materials beyond the capabilities of air permeability, such as soil samples, wet filters, permeability to different fluids (e.g. N2 or O2), and the like.

The operation of a fluid permeameter should be identical to the operation of the standard construction of the permeameter. The minor operational changes primarily govern fluid flow, specifically maintaining the level of feed fluid either from a recycling reservoir or from a reserve source. In addition, the pressure of the fluid against the flow surface of the samples (external to testing tubes) should be maintained constant to prevent erroneous differential permeability values.

In situations where permeability samples cannot be tested in a laboratory environment, and where samples are restricted by dimensions of extensive distance, a Large-Scale permeability measurement is applicable. Large-Scale air/fluid permeability testing, which might apply to more permanent-type production line or manufacturing process based testing, requires attention to be paid to the even distribution of pressure at the entrance (bottom in illustrations) of the testing tube. In order to ensure the even distribution of flow, the source "reservoir" pipes need to be wide enough that the pressure drop from friction along the outside is negligible. This would call for larger pipes as the distance between tubes increases.

In addition, the entrance to the testing tube should be near the center of the tube where the distribution will be equal. The use of a plenum similar to industrial heating and cooling methods would also be sufficient for testing. Further adjustments might be made by multiplying the data readings on the lower pressure tube by a factor of the change in pressure between the entrance points on the reference and test pipes.

In Large-Scale permeability testing, a number greater than two test pipes may exist. The permeometer will continue to function as long as the tubes are arranged in a manner that ensures even distribution of pressure. Approaches include the comparison of tubes in pairs (and preventing flow in the idle testing tubes) to minimize the required pressure, or the management of a large and even pressure reservoir to guarantee equal pressure at all test points.

General operation of a large-scale permeability measurement system should be generally identical to the standard method. The major difference is that active management is needed to monitor and adjust the tubes being utilized for testing purposes. Additional attention needs to be paid to the even flow of pressure at the entrance point to each testing tube, and software or hardware adjustments might need to made in order to ensure a accurate experimental reading.

The invention thus provides a permeameter and method wherein environmental factors are eliminated in the testing of a sheet-like permeable membrane sample by either providing a known sheet-like permeable membrane reference sample to provide an accurate permeability measurement or measuring the percent change between test and reference samples.

While the above description contains much specificity, these should not be construed as limitations on the scope of the invention, but rather as exemplifications of one preferred embodiment thereof. Many other variations are possible. For example, eliminating the orifice plates, adding multiple orifice plates and changing the clamping device.

The invention provides a method of measuring permeability of a sheet-like permeable membrane sample such that all environmental factors are eliminated. The method is such that a change in local temperature does not change the measurement accuracy of permeability and that changes in air density, and the factors controlling air density, such as relative humidity, do not affect the accuracy of measurement.

The method may be used to measure the change in permeability between samples such as, a standard sample to a random sample; a particular area on a cloth or web to other spots on the same cloth or web; a particular area on a cloth or web to areas on another cloth or web; and two random samples.

The permeameter may be operated to maintain a pressure differential applied to gauges within their operational limits while increasing the distance between testing tubes by manipulating air flow transmission pipes and plenums.

The relative calculation time required for determining a reading of relative accuracy may be decreased by estimating a large portion of test values from a portion of small measurements;

The time required to reach an optimum fan speed for testing purposes may be reduced by using a value estimated by the user in a variety of forms, or by remembering the last value used to implement as the initial value, beginning with a fixed value upon start-up.

The Honeycomb method may be used for maintaining quasi-laminar flow throughout the permeometer;

For numerically integrating the measurement of differential permeability over time to obtain a final measurement of differential permeability that is precise to an arbitrarily high number of significant digits;

And for calculating the permeability of a sheet-like test sample at the limit of infinite clamping pressure by measuring the change in permeability while the applied clamping pressure is varied through a range of pressures.

What is claimed is:

1. A differential permeameter comprising;
   a pair of flow systems, each said flow system being disposed for a flow of fluid there through;
   a reservoir connected in common to said flow systems to receive a flow of fluid from each said system;
   a fan for drawing fluid through said systems into said reservoir;
   a pair of clamping devices, each said clamping device being disposed in a respective flow system to hold a porous sheet-like material sample across said respective system for a flow of fluid therethrough; and
   a pair of orifice plates, each said plate being disposed in a respective flow system between said clamping device and said reservoir to create a measurable pressure drop in a fluid passing therethrough.

2. A differential permeameter as set forth in claim 1 wherein each said plate is disposed in a respective flow system between said clamping device and said reservoir therein.

3. A differential permeameter as set forth in claim 1 which further comprises a pair of honeycomb structures, each said structure being disposed in a respective one of said systems between said orifice plate therein and said reservoir for passage of a fluid therethrough to effect a laminar andf steady flow of fluid therethrough.

4. A differential permeameter as set forth in claim 1 further comprising a dual motorized screw drive disposed between said systems and connected to and between said pair of orifice plates for simultaneous movement thereof to adjust an orifice size thereof.

5. A differential permeameter as set forth in claim 1 further comprising a first pressure transducer positioned in one of said systems to measure a pressure drop across a test sample in said one system, a second pressure transducer positioned in said one system to measure a pressure drop across said orifice plate therein, a third pressure transducer positioned in the other of said systems to measure a pressure drop across said orifice plate therein, a fourth pressure transducer for measuring a differential pressure between said systems and a computer connected to each said transducer to receive a signal therefrom indicative of the pressure measured thereby and to calculate a differential permeability value of a sample in said one system in dependence on said signals.

6. A method for determining the permeability of a test sample comprising the steps of;

placing a sheet-like reference sample of known permeability in communication with a reference fluid flow system;

placing a sheet-like test sample of unknown permeability in communication with a test fluid flow system;

supplying a fluid flow stream across both test and reference samples;

adjusting the pressure drop of the fluid flow stream across one or both samples to a fixed standard;

measuring the fluid flow through the test fluid flow system by measuring the pressure drop across a flow device within the test fluid flow system;

measuring the fluid flow through the reference fluid flow system by measuring the pressure drop across a flow device within the reference fluid flow system;

measuring a pressure differential between the test fluid system and the reference fluid system; and calculating the permeability of the test sample by using the pressure differential across the test fluid flow system, the known permeability of the test sample, and the fluid flow through both the test fluid flow system and the reference fluid flow system.

* * * * *